United States Patent [19]

Clausen et al.

[11] Patent Number: 4,629,467
[45] Date of Patent: Dec. 16, 1986

[54] USE OF P-UREIDOALKYLAMINO-NITROBENZENE DERIVATIVES IN HAIR DYEING COMPOSITIONS AND NEW P-UREIDOALKYLAMINO-NITROBENZENE DERIVATIVES

[75] Inventors: Thomas Clausen, Alsbach; Eugen Konrad, Darmstadt, both of Fed. Rep. of Germany

[73] Assignee: Wella Aktiengesellschaft, Darmstadt, Fed. Rep. of Germany

[21] Appl. No.: 767,277

[22] PCT Filed: Jan. 16, 1985

[86] PCT No.: PCT/EP85/00012

§ 371 Date: Aug. 14, 1985

§ 102(e) Date: Aug. 14, 1985

[87] PCT Pub. No.: WO85/03223

PCT Pub. Date: Aug. 1, 1985

[30] Foreign Application Priority Data

Jan. 26, 1984 [DE] Fed. Rep. of Germany ....... 3402519

[51] Int. Cl.$^4$ ...................... A61K 7/13; C07C 127/19; D06P 1/19; D06P 3/14
[52] U.S. Cl. .......................................... 8/414; 8/405; 8/407; 564/47
[58] Field of Search ............................................ 8/414

[56] References Cited

U.S. PATENT DOCUMENTS 3,629,330 12/1971 Brody et al. ........................ 564/440
3,642,423 2/1972 Bil et al. .............................. 564/441
3,697,215 10/1972 Kalopissis et al. ..................... 8/412
4,008,272 2/1977 Kalopissis et al. .................... 564/27

FOREIGN PATENT DOCUMENTS 1150445 4/1969 United Kingdom .
2104895 3/1983 United Kingdom .
2122199 1/1984 United Kingdom .

OTHER PUBLICATIONS

International Journal of Cosmetic Science 1982, vol. 4, 1982, pp. 25-35.

Colour Index, Third Edition, vol. 4, published by The Society of Dyers and Colourists.
Hair Dyes, J. C. Johnson, Noyes Data Corporation, 1973, pp. 3-91 and 113-139.
Cosmetics, Science and Technology (1957), Interscience Publishers Inc., N.Y. pp. 503-511.

*Primary Examiner*—A. Lionel Clingman
*Attorney, Agent, or Firm*—Michael J. Striker

[57] ABSTRACT

Use of 1-ureidoalkyl amino-4-nitrobenzene compounds of formula I

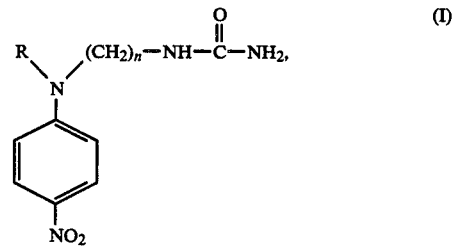

whereby R denotes hydrogen or an hydroxyalkyl residue with 2 to 4 carbon atoms and n a whole number of 2 to 4, as a direct dyeing hair dye in hair dyeing compositions. The dye agents of the formula I have very favorable toxicological characteristics. They deliver pure lemon yellow dyes with a high dye depth and are resistant against bases and reduction agents. A further object of the invention are new compounds of formula II

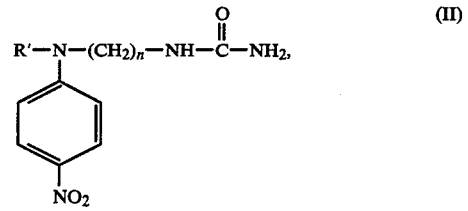

whereby R' denotes an hydroxyalkyl residue with 2 to 4 carbon atoms and n is a whole number from 2 to 4.

6 Claims, No Drawings

USE OF P-UREIDOALKYLAMINO-NITROBENZENE DERIVATIVES IN HAIR DYEING COMPOSITIONS AND NEW P-UREIDOALKYLAMINO-NITROBENZENE DERIVATIVES

It is an object of the invention to use nitro dyes for hair dyeing, whereby p-ureidoalkylamino-nitrobenzene derivatives in hair dyeing compositions are used as well as new p-ureidoalkylamino-nitrobenzene derivatives.

Nitro dyes are nowadays widely used in hair dyeing compositions. They are used in oxidation hair dyeing compositions as additions for generating natural or modern dye nuances. By combining of a plurality of differently dyed nitro dye compounds it is also possible to produce hair dyes which are able to dye the hair in natural to modern nuances without the use of oxidation agents.

For example, by combining an orange dye with a blue coloring nitro dye a natural appearing brown coloring may be obtained. However, it is also possible to achieve a similar result with a yellow coloring nitro dye substance.

Therefore, special nitro dye substances are required which are able to color the hair in an intensive pure lemon yellow which must be free from red constituents. Moreover, many other requirements are necessary. The nitro dye substances must be unobjectionable with respect to toxicological and dermatological requirements. Their use in oxidation hair dyes presumes that they are stable in the presence of hydrogen peroxide in an alkaline solution. Furthermore, they should be stable with respect to reduction agents which very often are constituents of oxidation hair dyes. Furthermore, a good light, acid and friction genuiness is required for the generated hair coloring. Furthermore, the nitro compounds should be able to be made very simply and cost effective.

The substituted amino-nitrophenoles which are heretofore described in the literature for a yellow coloring of the hair fulfill the aforementioned requirements only insufficiently. The 4-nitro-3-(2'-hydroxyethyl amino)-phenol described in the International Journal of Cosmetic Science 1982, pages 25–35 results in a lemon yellow coloring, but it is rather weak in its color. Two further isomers, namely the 4-nitro and the 5-nitro-2-(2'-hydroxyethyl amino)-phenol are not yellow coloring but orange coloring nitro dyes with interfering red constituents (see DE-PS 928,909 and DE-OS 3 231 455). The latter mentioned nitro dye is very pH-sensitive and shows undesirable color changes in acid or alkaline effects.

Further known yellow nitro color substances are the o- and p-nitroaniline derivatives mentioned in the DE-AS 1,619,393. These compounds substantially fulfill the requirements when applied, but are unsatisfactory with respect to the physiological characteristics.

Surprisingly it had been found that the aforementioned disadvantage can be overcome by using a 1-ureidoalkyl amino-4- nitrobenzene compound of the general formula I

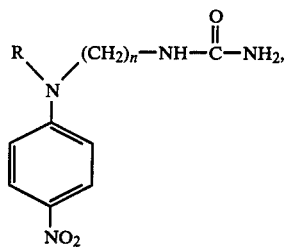

wherein R represents hydrogen or a hydroxy alkyl residue with 2 to 4 carbon atoms and n a whole number of 2 to 4 as a dye in hair dye compositions.

The discovery that compounds of the general formula I do fulfill all requirements necessary for yellow coloring nitro dyes used in hair dyeing compositions is very surprising because a compound of the general formula I with R=H and n=2 is already known from DE-OS 1,945,451 as a preliminary stage for the synthesis of the recommended compound N-(β-ureidoethyl)-paraphenylene diamine as a color base for oxidation hair dyes.

The dyes of the formula I which are described for the inventive application, the ones wherein R denotes a hydroxy alkyl residue with 2 to 4 carbon atoms are new.

Therefore, a subject matter of the present invention are also new 1-[N-hydroxy alkyl), N-(ureidoalkyl)-amino]-4-nitrobenzenes of the general formula II

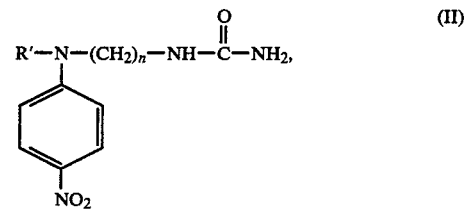

whereby R' constitutes a hydroxy alkyl residue with 2 to 4 carbon atoms and n a whole number of 2 to 4.

These compounds are characterized by an improved water solubility in contrast to the ones of formula I with R=H.

The p-ureidoalkyl amino-nitrobenzenes of the formula I (which include the new compounds of the formula II) may be made from inexpensive preliminary steps as follows:

Based on p-chloro-or p-fluoro nitrobenzene III a nucleophilic exchange of the halogene with an alkylene diamine IV is performed in accordance with the following reaction scheme, whereby a good yield of the aminoalkyl nitroaniline V is obtained. This is then transferred into the desired p-ureidoalkyl amino nitrobenzene of the formula I in an acid solution.

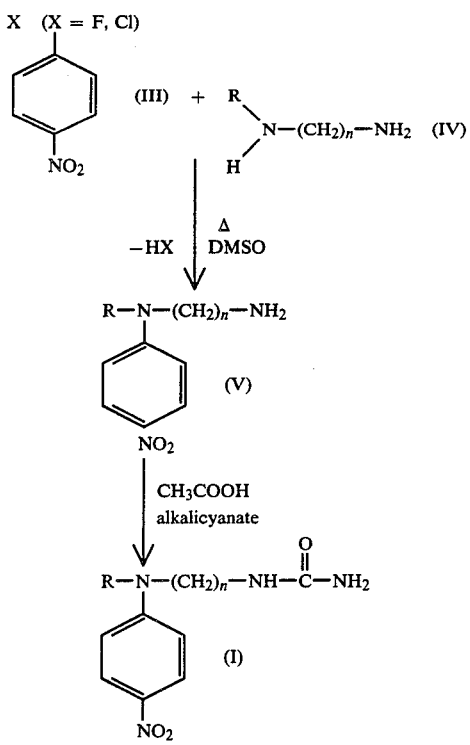

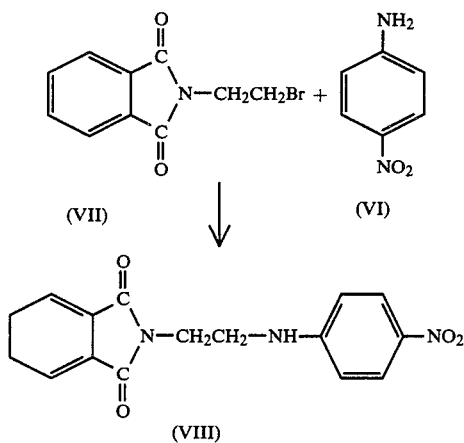

The aminoalkyl nitroanalines V which are required as an intermediary product may be preferably made by the Gabriel-reaction in that p-nitroanilin VI is reacted with the phthalimide derivatives of alkylene halides VII as mentioned in U.S. Pat. No. 3,332,948 and finally the amine is released from the phtalimide VIII.

The very good toxicological and physiological characteristics of the compounds in accordance with the general formula I are very surprising. For example, the two dyes 1-[(2'-ureidoethyl)-amino]-4-nitrobenzene and 1-[N(2'-ureidoethyl), N(2''-hydroxyethyl)-amino]-4-nitrobenzene are not mutagenic in the Amestest or only very weakly mutagenic and have a very low acute toxicity.

Particularly advantageous is the extremely high color density of the pure lemon yellow color tone which is obtained with the compounds of the formula I and also the stability with respect to a base, like ammonia and with respect to reduction agents like, for example, ascorbie acid, so that a use in oxidation hair dyes is also made possible.

The subject invention also relates to compositions for dyeing of hair with a dye substance content and for hair dyes with the usual additives, characterized in that it contains a p-ureidoalkyl amino-nitrobenzene compound in accordance with formula I.

The compositions in accordance with the invention relate to compositions for dyeing of hair and also such which may be used without an adding of oxidation agents, as well as such wherein the addition of an oxidation agent is required.

In the first mentioned hair dyes without any oxidation it refers to those ones, which may contain other dyes which can be directly applied to the hair in addition to the ones stated in the formula I. Of these known dyes for coloring the hair the following classes may be mentioned by way of example.

Aromatic nitro dyes (for example 1,4-diamino-2-nitrobenzene and the derivatives thereof), azo dyes (for example Acid Brown 4, C.I. 14 805), anthrachinon dyes (for example, disperse violet 4, C.I. 61 105), triphenyl methane dyes (for example Basic Violet 1, C.I. 42 535), whereby the dyes of these classes may have an acid, nonionic or basic character, depending on the type of their substitutents. Further dyes which can be directly applied on the hair are described in the book of J. C. Johnson, Hair Dyes "Noyes Data Corp. Park Ridge (USA) (1973), pages 3–91 and 113–139 (ISBN: 0-8155-0477-2).

With these inventive hair dyes which contain compounds of the formula I in a mixture with the aforementioned dyes modern blond and brown tones of an excellent stability may be obtained in addition to the pure fashion tones.

The type of preparation of the hair dyes described here on the basis of directly to be applied dyes onto the hair may be a solution, in particular a aqueous or aqueous alcoholic solution, for example. Preferred types of preparations are a creme, a gel or an emulsion, whereby it can be also sprayed with a mixture of a propellant or by means of a pump.

The dyes of the stated formula I in these dye compositions without an addition of oxidation agents should be contained in a concentration of about 0.01 to 1.0% by weight, preferably 0.01 to 0.5% by weight. The total content of the directly applied dyes is in a limit of about 0.01 to 3.0% by weight. The pH-value of these dyes is in the area of 3 to 10.5, in particular at pH 7.5 to 9.5, whereby the adjustment of the desired alcaline pH-value is mainly performed with ammonia, however also with organic amines like, for example, monoethanolamine or triethanolamine.

The application of the same is performed in a common manner by applying an amount of the dye onto the hair which is sufficient, whereby it remains in contact with the hair for a time period, about 5 to 30 minutes. Subsequently a rinsing is performed with water, if need be, also with an aqueous solution of a weak organic acid, is then rinsed and dried. For example, acetic acid, citric acid, tartaric acid and similar may be used as weak organic acid.

Naturally, the aforementioned described hair dyes without the oxidation agent addition may contain cosmetic polymerisates, whereby a fastening of the hair is achieved simultaneously with the coloring. Such substances are usually called toning fixers or color fixers.

Of the known polymerisates which are known to be used for this purpose in the cosmetic field we would like to mention, by way of example, the polyvinyl pyrrolidon, polyvinyl acetate, polyvinyl alcohol or polyacryl compositions like acrylic acid or methacrylic acid polymerisates, basic polymerisates of esters from these two acids and amino alcohols or the salts thereof or quaternisation products, polyacryl nitrile, polyvinyl lactame as well as copolimerisates made from such compositions like polyvinylpyrrolidonevinyl acetate and the like.

Also, natural polymers may be used, like chitosane (deacetylized chitine) or chitosan derivatives may be used for the mentioned purpose.

The polymerisates are contained in these compositions in the customary amount of from 1 to 5% by weight. The pH-values of the compositions are in a range of about 6.0 to 9.0.

The application of these hair dyes with additional fastening is performed in known and customary manner by wetting the hair with the fixer, fixing (place) the hair into a hairdo and subsequent drying.

Naturally, the aformentioned described hair dyes without the oxidation agent additive may contain other customary additives for hair dyes, for example, hair care agents, wetting agents, thickeners, softeners and perfume oils, as well as other customary additives which are stated in the following for oxidation hair dyes.

The subject matter of the invention also encompasses such hair dyes wherein the addition of an oxidation agent is required, as already stated before. They contain, in addition to the hair dyes in accordance with formula I and, if need be, the dyes which can be applied directly to the hair, still additional known oxidation dyes which require an oxidative development.

These oxidation dyes are mainly aromatic p-diamines and p-aminophenoles like, for example, p-toluylene diamine, p-phenylene diamine, p-aminophenole and similar compounds which for the purpose of shading the dyes are combined with so-called modifiers, for example, m-phenylene diamine, resorcinol, m-aminophenol and others.

Such known and customary oxidation dyes for hair dyeing are described, among others, in the book of E. Sagarin, "Cosmetics", Science and Technology (1957), Interscience Publishers Inc., New York, pages 503 etc., as well as in the book of H. Janistyn, "Handbuch der Kosmetika und Riechstoffe" (1973) pages 338 etc.

With mixtures of these oxidation dyes and the dyes in accordance with formula I modern blond and brown tones are obtained in addition to the pure fashionable tones.

The dyes in accordance with formula I are contained in these dyes with an oxidation agent additive in a concentration of about 0.01 to 1.0% by weight, preferably 0.05 to 0.5% by weight. The total weight of dyes in these dye compositions is about 0.1 to 5.0% by weight.

Oxidation hair dyes are generally alkalically adjusted, preferable to pH-values of about 8.0 to 11.5, whereby the adjustment is performed in particular with ammonia. However, other organic amines may also be used, for example, monoethanol amine or triethanol amine. Mainly, hydrogen peroxide and the addition compounds thereof are taken into consideration. The mode of preparation of the hair dyes can be the same as in hair dyes without oxidation agent additives. Preferably, it is in form of a creme or a gel.

Customary additives in cremes, emulsions or gels are, for example, solvents, like water, low aliphatic alcohols, for example, ethanol, propanol, isopropanol, glycerine or glycols, like ethylene glycol and propylene glycol, or also glycol ethers, furthermore wetting agents or emulsifiers from the classes of the anionic, cationic, amphoteric or nonionic surface active substances, like fatty alcohol sulfates, fatty alcohol ether sulfates, alkyl sulfonates, alkyl benzene sulfates, alkyl trimethyl ammonium salts, alkyl betaines, oxethylized fatty alcohols, oxethylized nonylphenoles, fatty acid alkanolamides, oxethylized fatty acid esters, furthermore thickeners, like higher fatty alcohols, bentonite, starch, polyacrylic acid, cellulose derivatives like carboxymethyl cellulose, alginates, vaseline, paraffin oil and fatty acids as well as caring agents, like lanoline derivatives, cholesterine, pantothenic acid and betain, furthermore perfume oils and complex formers. The mentioned constituents are used in the amounts customary for such purposes, for example, the wetting agents and emulsifiers in concentrations of about 0.5 to 30% by weight, while the thickeners may be present in an amount of about 0.1 to 25% weight in the preparations.

The application of the mentioned preparations, wherein the addition of an oxidation agent is required, is performed in a customary manner in that the hair dyes are admixed with the oxidation agent before the treatment and that an amount of the mixture sufficient for coloring the hair, generally about 50 to 150 ml, is applied to the hair. After a sufficient reaction time for the hair dyeing, which customarily is from 10 to 45 minutes, a rinsing is performed with water, if need be, subsequently with the aqueous solution of a weak organic acid, for example, citric acid or tartaric acid and then rinsed.

With respect to the color possibilities the hair dyes in accordance with the invention offer a wide variety of color shading depending on the type and composition of the dye components, extending from natural to highly fashionable, shining shadings. Thereby, the dyes are used either in conjunction with hydrogen peroxide or without any oxidation agent, depending on their composition.

The following examples should explain the subject matter of the invention without limiting it thereto.

EXAMPLES FOR COMPOSITIONS TO DYE THE HAIR

Example 1: Liquid hair dye compositions

| | |
|---|---|
| 0.10 g | 1-[(2'-ureidoethyl)-amino]-4-nitrobenzene |
| 0.50 g | hydroxyethyl cellulose |
| 5.00 g | lauryl alcohol-diglycol ether sulfate-sodium salt, 28% aqueous solution |
| 15.00 g | isopropyl alcohol |
| 0.03 g | ammonia, 25% aqueous solution |
| 79.37 g | water |
| 100.00 g | |

30 ml of the liquid hair dye composition of the aforementioned composition are applied to white human hair with a reaction time of 10 minutes. The hair has a shining yellow color after rinsing with water and after drying.

Example 2: Dye fixer

```
 0.05 g 1-[2'-ureidoethyl)-amino]-4-nitrobenzene
 2.00 g polyvinylpyrrolidone
 0.10 g glycerine
40.00 g isopropyl alcohol
57.85 g water
100.00 g
```

White human hair were set for a hairdo with 20 ml of the aforementioned fastening dye solution and dried. The hair is colored in a shining yellow and fastened.

Example 3: Oxidation hair dye composition

```
 0.05 g 1-[(2'-hydroxyethyl),N—(2''-ureidoethyl)-amino]-
        4-nitrobenzene
30.00 g oleic acid
15 00 g isopropyl alcohol
18.00 g ammonia, 25%
 0.20 g disodium salt of the ethylene diamine-tetraacetic
        acid
 0.30 g ascorbic acid
 0.40 g p-toluylene diamine-sulfate
 0.15 g resorcinol
 0.03 g m-aminophenol
30.87 g water
100.00 g
```

50 ml of the aforementioned hair dye composition are admixed with 50 ml of a hydrogen peroxide solution (6%) shortly before use. Subsequently, the generated gel is applied to grey human hair and react thereon for 30 minutes. Thereafter, a rinsing with water is performed and the hair is dried. The hair has obtained a natural blond shade.

Example 4: Oxidation hair dye agent in form of a creme

```
 0.10 g 1-[(2'-ureidoethyl)-amino]-4-nitrobenzene
 1.50 g p-phenylene diamine
 0.50 g m-aminophenol
 1.00 g 3,5-diamino-2,6-dimethoxy pyridin-dihydro chloride
 0.30 g ascorbic acid
15.00 g cetyl alcohol
 3.50 g lauryl alcohol-diglycol ether sulfate-sodium salt
        (28% acqueous solution)
 6.00 g ammonia, 25%
72.10 g water
100.00 g
```

50 ml of the aforementioned hair dye composition are admixed with 50 ml of a hydrogen peroxide solution (6%) shortly before use. Subsequently, the mixture is applied to gray human hair and react thereon for 30 minutes at a temperature of 40° C. After rinsing the hair with water and subsequent drying the hair is colored in a deep black without a stain.

MANUFACTURING EXAMPLE

Stage 1: Manufacturing of 1-[N-(2'-aminoethyl), N-(2''-hydroxyethyl)-amino]-4-nitrobenzene 15.7 g (0.1 Mol) 4-nitrochlorobenzene and 30 g N-(2-hydroxyethyl)-ethylene diamine are dissolved in 20 ml dimethyl sulfoxide and heated for 4 hours to 140° C. Subsequently, the reaction mixture is poured onto ice and the insoluble reaction product is filtered off. After drying, a recrystalisation is performed in acetic ester. One obtains 12.0 g (53% of the theory) of the pure compound in form of yellow crystals which have a melting point of 126° C.

Stage 2: Manufacturing of 1-[N-2'-hydroxyethyl), N-2''-ureidoethyl)-amino]-4-nitrobenzene 12.0 g of the nitrobenzene derivative from stage 1 are dissolved in 20 ml glacial acetic acid by heating. After removing the heating bath 5.2 g potassium cyanate is added in portions. Subsequently there is a heating process for 15 minutes and a diluting with water. The desired ureido compound precipitates. It is filtered off and recrystallized from water. One obtains 4.0 g (28% of the theory) of the pure ureido compound with a melting point of 196° C.

Proton-nuclear resonance spectrum (NMR)

| Data in δ (ppm) | Standard:tetramethyl silane<br>Solvent:hexadeuterized<br>dimethyl sulfoxide (DMSO-$d_6$) |
|---|---|
| 8.00 | (Doublet, 3-H, 5-H, J = 9, 5 Hz) |
| 7.32 | (wide, NH) |
| 6.68 | (Doublet, 2-.H, 6-H, J = 9, 5 Hz) |
| 5.88 | (Singlet, severe, $NH_2$) |
| 4.84 | (Triplet, OH, J = 5 Hz) |
| 3.60–3.15 | (Multiplet $CH_2$) |

We claim:

1. Process to dye hair comprising applying thereto an effective amount of a 1-ureido alkyl amino-4-nitrobenzene compound of the general formula I

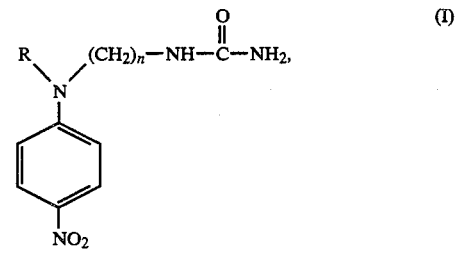

wherein R represents hydrogen or a hydroxy alkyl residue with 2 to 4 carbon atoms and n a whole number of 2 to 4 as a dye in hair dye compositions.

2. Compositions for dyeing of hair with a dye agent content and additives which are customary for hair dye agents, characterized in that it contains 0.01 to 1.0% of weight of a 1-ureidoalkylamino-4-nitrobenzene compound of the formula I

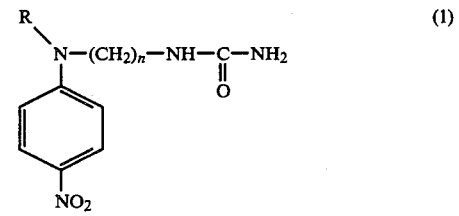

wherein R represents hydrogen or a hydroxy alkyl residue with 2 to 4 carbon atoms and n a whole number of 2 to 4.

3. Compositions in accordance with claim 2, characterized in that it contains 0.01 to 1.0% by weight 1[(2'-ureidoethyl-)amino]-4-nitrobenzene.

4. Compositions in accordance with claim 2, additionally containing at least one of the known oxidation hair dye agents.

5. Compositions in accordance with claim 4, characterized in that it has a pH-value of 8.0 to 11.5.

6. Composition in accordance with claim 2 with additional hair setting ability, comprising in an aqueous-alcoholic solution a direct dye and at least one polymer customary in cosmetics.

* * * * *